(12) United States Patent
Geiger et al.

(10) Patent No.: US 10,274,807 B2
(45) Date of Patent: Apr. 30, 2019

(54) OPTICAL QUANTIFICATION OF INTERFACIAL CHARGE STATES

(71) Applicants: Northwestern University, Evanston, IL (US); Battelle Memorial Institute, Columbus, OH (US); The Trustees of Columbia University in the City of New York, New York, NY (US)

(72) Inventors: Franz M. Geiger, Evanston, WI (US); Paul E. Ohno, Evanston, IL (US); Hong-fei Wang, Richland, WA (US); Kenneth B. Eisenthal, New York City, NY (US)

(73) Assignees: Northwestern University, Evanston, IL (US); Battelle Memorial Institute, Columbus, OH (US); The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/834,250

(22) Filed: Dec. 7, 2017

(65) Prior Publication Data

US 2018/0164657 A1   Jun. 14, 2018

Related U.S. Application Data

(60) Provisional application No. 62/431,643, filed on Dec. 8, 2016.

(51) Int. Cl.
*G02F 1/35* (2006.01)
*G01N 21/63* (2006.01)
(Continued)

(52) U.S. Cl.
CPC ......... *G02F 1/3532* (2013.01); *G01N 21/636* (2013.01); *G01N 21/84* (2013.01);
(Continued)

(58) Field of Classification Search
CPC .......... G02F 1/3532; G02F 1/355; G02F 1/37; G02F 1/377; G01N 21/636
See application file for complete search history.

(56) References Cited

U.S. PATENT DOCUMENTS 5,294,289 A * 3/1994 Heinz ................... B24B 37/013
                                                           118/712
7,158,284 B2 * 1/2007 Alles ....................... G01N 21/63
                                                          324/754.23
(Continued)

OTHER PUBLICATIONS

Corn et al., Optical Second Harmonic Generation as a Probe of Surface Chemistry, Chem. Rev. 94 (1994), pp. 107-125.
(Continued)

*Primary Examiner* — Daniel Petkovsek
(74) *Attorney, Agent, or Firm* — Bell & Manning, LLC

(57) ABSTRACT

Methods of generating second harmonic generation (SHG) signals from interfaces formed with, or formed over, a noncentrosymmetric material, e.g., α-quartz, are provided. The methods make use of the noncentrosymmetric material as an internal phase reference for the determination of a variety of interfacial electrostatic parameters, including interfacial potential, interfacial charge density, and the sign of the interfacial charge (i.e., net positive or net negative).

15 Claims, 9 Drawing Sheets

(51) Int. Cl.
G02F 1/355 (2006.01)
G02F 1/377 (2006.01)
G01N 21/84 (2006.01)

(52) U.S. Cl.
CPC ............... *G02F 1/35* (2013.01); *G02F 1/355* (2013.01); *G02F 1/377* (2013.01)

(56) References Cited

U.S. PATENT DOCUMENTS

| | | | | |
|---|---|---|---|---|
| 7,339,681 | B2* | 3/2008 | Su | G01N 21/21 356/491 |
| 9,778,177 | B2* | 10/2017 | Roke | G01N 21/47 |
| 2005/0118731 | A1* | 6/2005 | Salafsky | B82Y 30/00 436/518 |
| 2013/0288271 | A1* | 10/2013 | Salafsky | G01N 33/68 435/7.8 |

OTHER PUBLICATIONS

Sarah A. Saslow, Chapters 2 and 5 of Geochemical Interfaces and Metal Contaminant Transport Studied by Second Harmonic Generation, Northwestern University, Jul. 2015.
Franz Geiger, Counterfactual-enabled molecular spectroscopy from computation and experiment, Presentation at Pacifichem 2015, Dec. 15, 2015.
Dadap et al., Lasers in Physics: Second-Harmonic Spectroscopy, Research Gate online publication, Nov. 20, 2014, pp. 1-46.
Kenneth B. Eisenthal, Second Harmonic Spectroscopy of Aqueous Nano- and Microparticle Interfaces, Chem. Rev. 106, Mar. 30, 2006, pp. 1462-1477.
Nowakowski et al., Time-resolved phase-sensitive second harmonic generation spectroscopy, The Journal of Chemical Physics 142, Feb. 23, 2015, pp. 084201-1-084201-8.
Ostroverkhov et al., New Information onWater Interfacial Structure Revealed by Phase-Sensitive Surface Spectroscopy, Physical Review Letters 94, Feb. 2, 2005, pp. 046102-1-046102-4.

* cited by examiner

OPTICAL QUANTIFICATION OF INTERFACIAL CHARGE STATES

CROSS-REFERENCE TO RELATED APPLICATIONS

The present application claims priority to U.S. provisional patent application No. 62/431,643 that was filed Dec. 8, 2016, the entire contents of which are hereby incorporated by reference.

REFERENCE TO GOVERNMENT RIGHTS

This invention was made with government support under DE-AC05-76RL01830 awarded by the Department of Energy and CHE1057483, CHE1464916 awarded by the National Science Foundation. The government has certain rights in the invention.

BACKGROUND

The strength of the second harmonic electric field, $E_{2\omega}$, that is produced at charged interfaces is a function of the incident fundamental electric field, $E_\omega$, the second order susceptibility of the interface, $\chi^{(2)}$, the zero-frequency electric field corresponding to the interfacial potential produced by surface charges, $\Phi(0)$, and the third-order susceptibility, $\chi^{(3)}$, according to[1-6] the following equation:

$$\sqrt{I_{SHG}} \propto E_{2\omega} \propto \chi^{(2)} E_\omega E_\omega + \chi^{(3)} E_\omega E_\omega \Phi(0)$$

Early work, in which the relative phase of the terms contributing to the second harmonic generation (SHG) intensity was included[7], shows that when the wavelength of the fundamental and second harmonic photons are far from electronic and vibrational resonance, $\chi^{(2)}$ and $\chi^{(3)}$ are real, though they may differ in sign[7,8]. Yet, phase information has not been recovered in traditional SHG detection schemes, as they only collect the square modulus of the signal. While phase information from SHG and vibrational sum frequency generation (SFG) signals can be obtained through coherent interference of the signal of interest with an external[9-16] or internal[7,18] phase standard, applications of such reference techniques to determine the phase of SHG signals generated at buried interfaces, such as charged oxide/water interfaces, is challenging due to the presence of dispersive media on both sides of the interface. Additionally, the interface between water and α-quartz, the most abundant silicate mineral in nature[19-21], has been theoretically predicted to produce a more ordered interfacial water layer than amorphous silica[22-24], though this has not yet been probed using even traditionally detected SHG, as the noncentrosymmetric bulk generally produces second harmonic signals that overpower surface SHG signals by orders of magnitude to the point where the surface signal is indistinguishable from the bulk response.

BRIEF DESCRIPTION OF THE DRAWINGS

Illustrative embodiments of the invention will hereafter be described with reference to the accompanying drawings, wherein like numerals denote like elements.

FIG. 1A depicts an external reflection geometry and a flow cell used in the Examples. FL=focal lens; RL=recollimating lens. FIG. 1B is a top view of right-handed z-cut α-quartz as placed across the plane of incidence. The "+" and "−" signs depict the sign of the bulk quartz phase. FIG. 1C depicts the phase-referencing process used to unveil the newly identified term $i\chi^{(3)}\Phi(0)$.

DETAILED DESCRIPTION

Methods for probing interfaces based on the technique of second harmonic generation (SHG) spectroscopy are provided. The methods enable the determination of a variety of interfacial electrostatic parameters, including the absolute interfacial potential, the absolute interfacial charge density, and the absolute sign of the interfacial charge (i.e., net positive or net negative). Conventional SHG methods can provide, e.g., charge densities and potentials, but not the sign of the charge and the sign of the potential. To address this limitation, such conventional approaches involve the use of external phase references which require overlapping signal from the external phase reference with the interfacial signal in both space and time, which is both challenging and sensitive to phase drift. Alternative conventional approaches include supplementing the conventional SHG methods with additional measurements using streaming potential apparatuses and X-ray photoelectron spectroscopy (XPS), both which require additional time, are expensive, and require complex instrumentation. By contrast, the present methods enable a quicker, more cost-effective and more comprehensive approach to analyzing interfacial electrostatics, including enabling the direct and unambiguous determination of the absolute sign of the interfacial charge, e.g., in a single charge-screening experiment.

In embodiments, a method of probing an interface comprises illuminating an interface formed with a noncentrosymmetric material or disposed above the noncentrosymmetric material with light having a frequency $\omega$ under conditions sufficient to generate a second harmonic generation (SHG) signal having frequency $2\omega$ and detecting the SHG signal. By "interface" it is meant the area of contact between two different materials. One of these materials may be the noncentrosymmetric material itself such that the interface is that formed between a surface of the noncentrosymmetric material and a surface of a different material. This different material may be a liquid, e.g., water, aqueous mixture, aqueous solution, etc. Alternatively, as further described below, the interface formed between two different materials (e.g., solid/liquid) may be disposed above the surface of the noncentrosymmetric material. In either case, the liquid may comprise a variety of components, e.g., acids, bases, salts, etc., depending upon the desired conditions, or even other analytes capable of interacting (e.g., binding) with a material of the interface. As further described below, the noncentrosymmetric material is characterized by its orientation angle with respect to a reference axis. The illumination and detection steps may be carried out at a selected (i.e., predetermined) orientation angle.

Figure 1A:
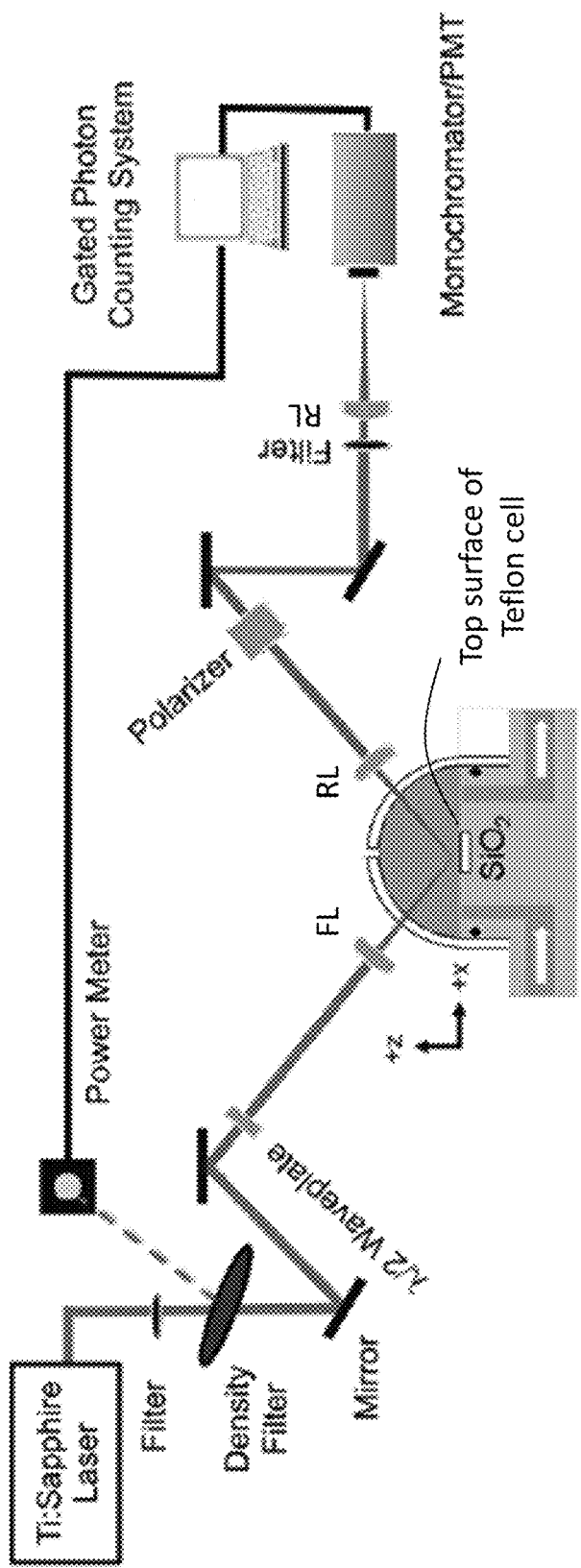
FIGS. 1A-1C illustrate an experimental setup for carrying out a method of probing an interface according to an illustrative embodiment.
Figure 1B:
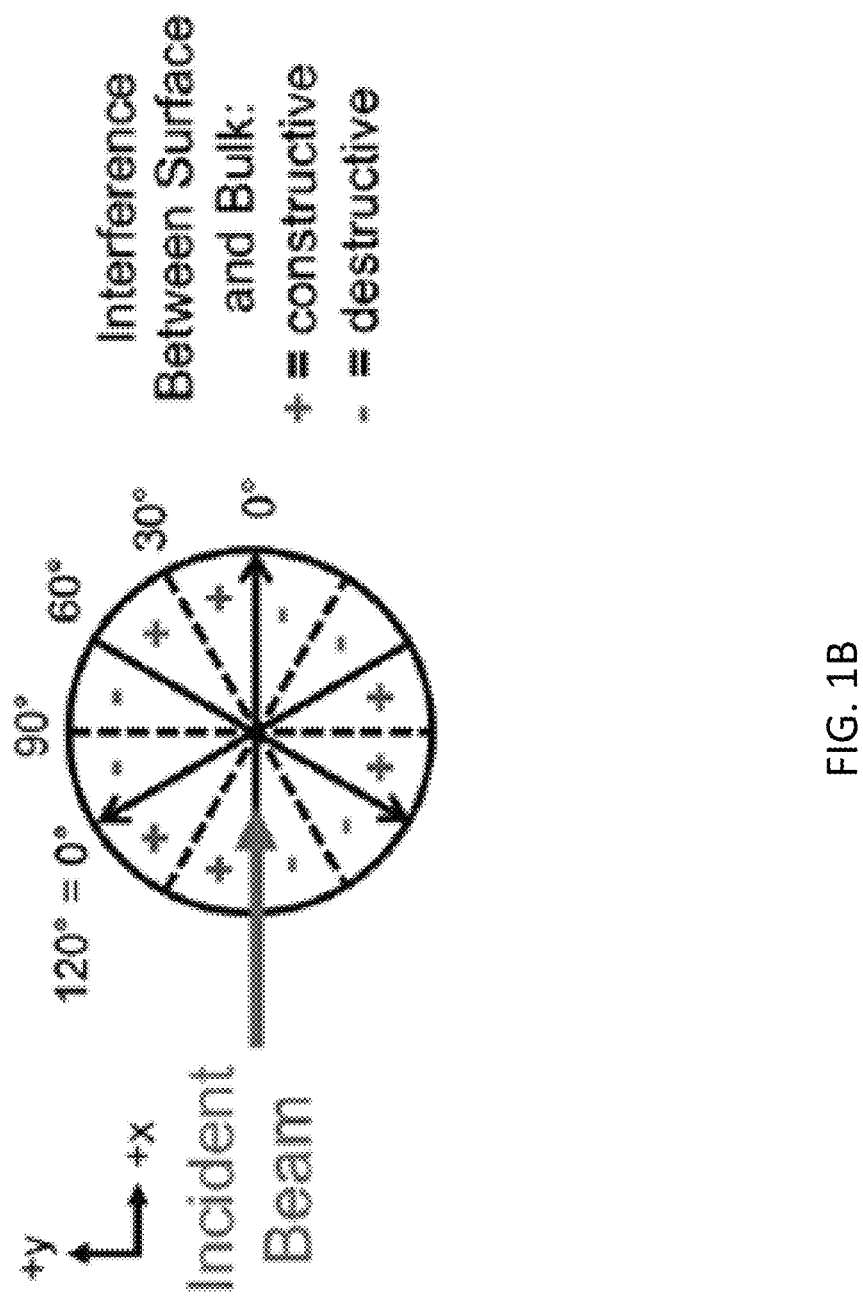
Figure 1C:
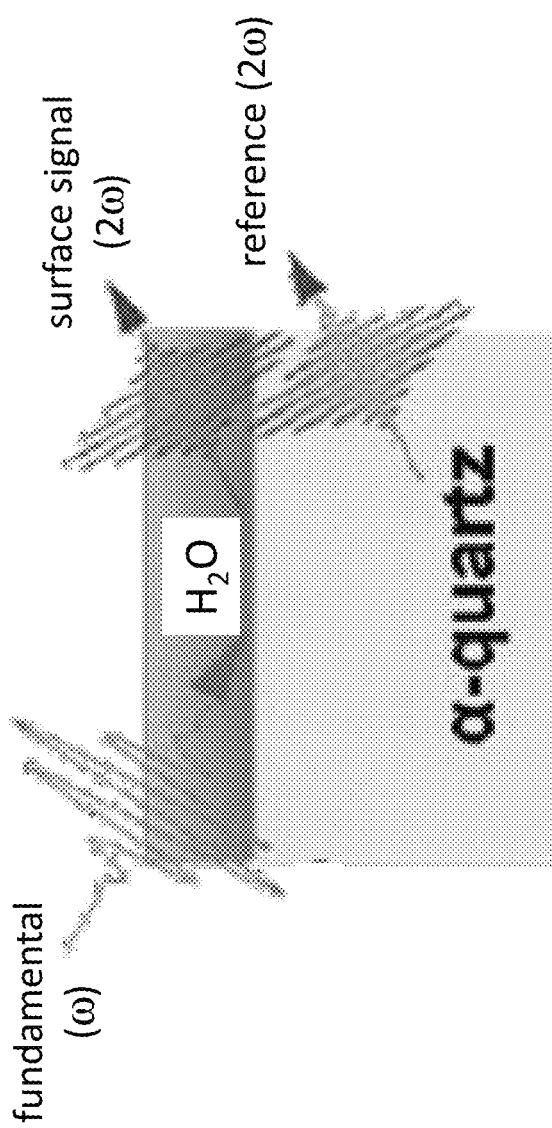

As illustrated in FIG. 1C, unlike centrosymmetric materials, the noncentrosymmetric materials used in the present methods will also produce a bulk second harmonic signal (reference ($2\omega$)), in addition to the second harmonic signal originating from the interface (surface signal ($2\omega$)), i.e., the interface formed with the noncentrosymmetric material or the interface disposed above the noncentrosymmetric material. Both contribute to the detected SHG signal. However, as further described below, the inventors have found that the bulk second harmonic signal undergoes interference with the interfacial second harmonic signal and that this interference depends upon the orientation angle of the noncentrosymmetric material with respect to the reference axis. The inventors have exploited this phenomenon to use the noncentrosymmetric material as an internal phase reference in the present methods, e.g., for directly determining the sign of the interfacial charge.

A variety of noncentrosymmetric materials may be used, including noncentrosymmetric oxides such as those described in Halasyamani, P. S., et al., Noncentrosymmetric Oxides, *Chem. Mat.* 10, 2753-2769 (1998), which is hereby incorporated by reference in its entirety. An illustrative noncentrosymmetric material is $\alpha$-quartz.

Figure 6A:
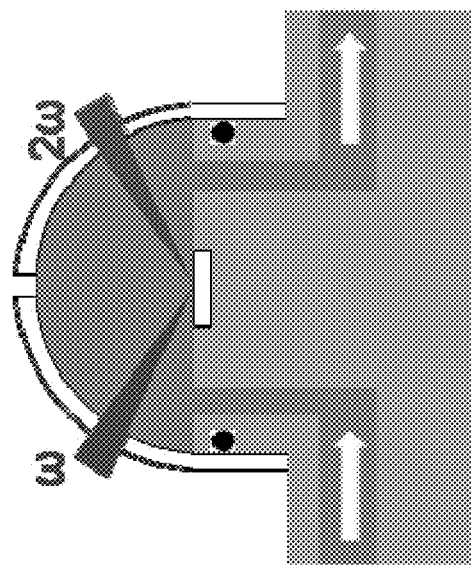
FIG. 6A is a schematic depiction of a total-internal or near total-internal reflection geometry.
Figure 6B:
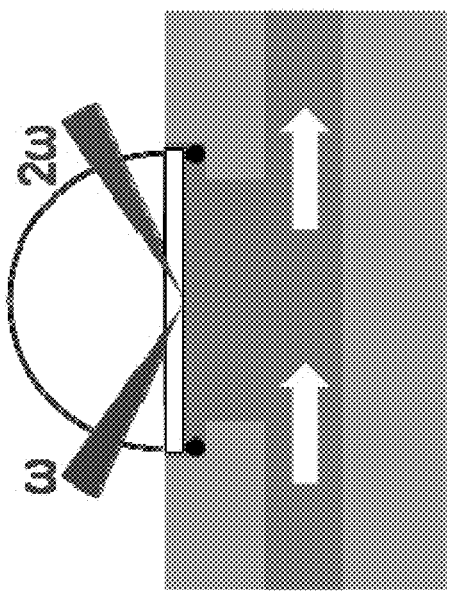
FIG. 6B is a schematic depiction of the external reflection geometry. Internal reflection produces a higher signal intensity due to higher Fresnel coefficients. (See Li, B., et al. Sum Frequency Generation of Interfacial Lipid Monolayers Shows Polarization Dependence on Experimental Geometries. *Langmuir* 32, 7086-7095 (2016). Fused silica hemispheres are used in order to ensure high transmission coefficients and retain the input polarization at any input angle. To study surfaces besides fused silica in this geometry, disks of material such as muscovite (Gomez, S. A. S. et al, Precipitates of Al(III), Sc(III), and La(III) at the Muscovite-Water Interface. *J. Phys. Chem. A* 118, 10974-10981 (2014)) can be clamped between the hemisphere and the aqueous phase. However, as discussed in the Examples, the non-centrosymmetric nature of α-quartz produces an overwhelmingly large bulk signal in this geometry. Thus, the external reflection geometry may be used, in which the light does not propagate through the non-centrosymmetric material.

The form of the noncentrosymmetric material used in the present method is not particularly limited. For example, a substrate formed entirely of the noncentrosymmetric material may be used. (See, e.g., the $SiO_2$ wafer in FIG. 1A and the portion of this wafer labeled "$\alpha$-quartz" in FIG. 1C.) Alternatively, the noncentrosymmetric material may be provided as a thin film on a support substrate, the support substrate which may be formed of an optically transparent centrosymmetric material, e.g., fused silica. This enables illumination geometries in which the illumination light propagates through the solid (i.e., the support substrate coated with the film of noncentrosymmetric material) instead of the other material (e.g., aqueous solution). Such an illumination geometry may be referred to as an internal reflection geometry. (See e.g., FIG. 6A.) However, an external reflection geometry (see FIG. 1A and FIG. 6B and further described below), may also be employed when using a thin film of a noncentrosymmetric material on a support substrate.

As described above, the interface may be that formed between two different materials and disposed above the noncentrosymmetric material. By way of illustration, thin film deposition techniques such as atomic layer deposition, electron beam deposition, spin-coating, or surface functionalization techniques (e.g., silane chemistry) may be used to provide thin films of a variety of materials (e.g., polymers) on the surface of the noncentrosymmetric material. The present method may be used to study interfaces formed between the surface of such thin films and a surface of another material such as a liquid, e.g., water, aqueous mixture, aqueous solution, etc. as described above. The thin film may be referred to as a sample and its upper surface (opposite to that in contact with the noncentrosymmetric material) may be referred to as the sample surface.

Figure 5A:
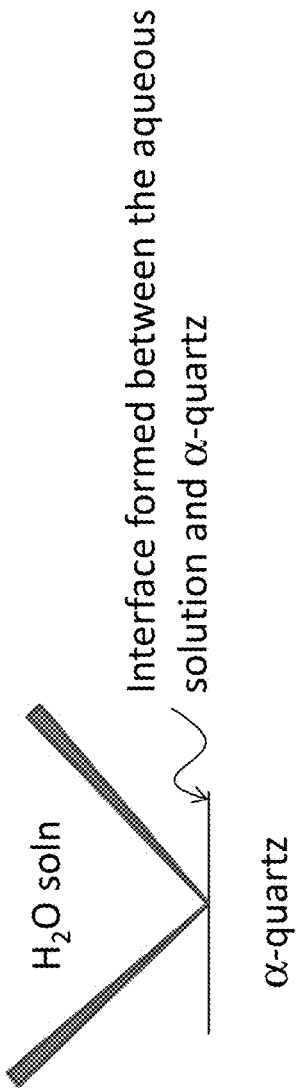
FIG. 5A is a schematic of the illumination of an interface formed between an aqueous solution and the surface of α-quartz to generate a SHG signal.
Figure 5B:
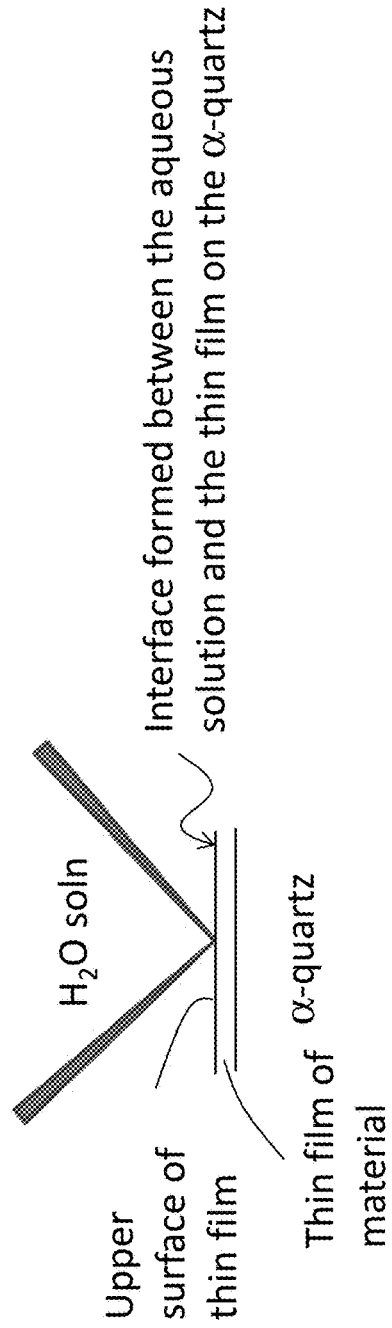
FIG. 5B is a schematic of the illumination of an interface formed between an aqueous solution and the upper surface of a thin film of a material disposed on the surface of α-quartz to generate a SHG signal. This experimental set-up may be used to determine the charge on the upper surface of the thin film as well as the orientation of water molecules at the interface.

Two illustrative interfaces are shown in FIGS. 5A and 5B. The top image (FIG. 5A) shows an interface formed between the upper surface of the noncentrosymmetric material ($\alpha$-quartz) and an aqueous solution. The bottom image (FIG. 5B) shows a thin film of a material disposed on the upper surface of the $\alpha$-quartz and an interface formed between the upper surface of the thin film and the aqueous solution. In the latter embodiment, thin films of a few nanometers are expected to interact with water molecules in a similar fashion to a bulk quantity of the thin film material while still allowing for the coherent interaction between the bulk second harmonic signal and the interfacial second harmonic signal described above.

In embodiments, the light used in the method is non-resonant light, by which it is meant that the selected frequency $\omega$ is off-resonance with a transition (e.g., an electronic, vibrational, etc. transition) in an interfacial component (e.g., water molecules at the interface of the sample and the noncentrosymmetric material).

A system for carrying out the present methods is shown in FIG. 1A and further described in the Examples, below. Briefly, the system utilizes a high repetition rate, low pulse energy femtosecond Ti:Sapphire oscillator. An illustrative oscillator is the model Mai Tai from Spectra-Physics generating 120 fs pulses at 800 nm at a repetition rate of 82 MHz. However, other lasers with similar specifications produce the same result. Prior to the sample stage, the beam is passed through a long-pass filter to remove any second harmonic co-propagating with the fundamental beam. The beam is then passed through a half-wave plate for polarization control, and focused onto the sample stage with a lens. The sample stage includes a Teflon cell that holds the substrates (e.g., α-quartz) horizontally, contains inlets and outlets for flow, and allows a hollow fused silica dome to be sealed over it with a Viton o-ring.

The reflected beam is recollimated with a lens, passed through a polarizer for output polarization control, passed through a 400 nm bandpass filter to remove the fundamental, and finally into a monochromator and photomultiplier tube. The photomultiplier tube signal is preamplified and counted by a gated photon counter (e.g., with the SR445A and SR400, Stanford Research Systems). A portion of the fundamental beam is picked off prior to the sample cell and continuously monitored by a power meter during acquisitions to allow for continuous normalization of signal intensity to power and minimize impact of laser power fluctuations. The signal is normalized by the square of the input power.

As shown in FIG. 1A, the illumination geometry is such that the illumination light propagates through the material (the aqueous solution) on the noncentrosymmetric material (the α-quartz substrate), rather than through the noncentrosymmetric material itself. This illumination geometry may be referred to as an external reflection geometry, by contrast to the internal reflection geometry shown in FIG. 6A. As further described in the Examples, below, SHG signals obtained using the external reflection geometry of FIG. 1A were significantly more sensitive to the interface relative to the bulk as compared to the internal reflection geometry of FIG. 6A.

FIG. 1B illustrates the orientation angle of the noncentrosymmetric material, in this embodiment, the α-quartz substrate. A α-quartz substrate (as well as other noncentrosymmetric materials) may be characterized by its x-, y-, and z-axes. (The location and orientation of the x-axis of a α-quartz substrate can be determined as described in the Examples, below.) As described above, the α-quartz substrate is held horizontally in the sample stage, i.e., so that the plane defined by the x- and y-axes of the α-quartz substrate is parallel to the top surface of the Teflon cell and the z-axis of the α-quartz substrate is perpendicular to the top surface of the Teflon cell. To define a reference axis from which the orientation angle of the α-quartz substrate is measured, the α-quartz substrate may be rotated about its z-axis until the incoming laser beam is aligned parallel to the x-axis of the α-quartz substrate (i.e., the horizontal projection of the incoming laser beam is along the x-axis). The reference axis is that axis which is coincident with the x-axis of the α-quartz substrate in this configuration. Then, the orientation angle is the angle the α-quartz substrate is rotated about its z-axis clockwise relative to this reference axis. The orientation angle may be referred to as angle φ in the present disclosure.

As noted above, the illumination and detection steps of the present methods may be carried out at a selected orientation angle. The selected orientation angle may be that which maximizes the constructive interference of the bulk second harmonic signal and an interfacial second harmonic signal. By "maximizes" it is meant "substantially maximizes" such that the constructive interference does not be at its perfect maximum. In this case, the interfacial second harmonic signal may be from a reference interface formed between the noncentrosymmetric material and a reference material (e.g., pure water or an aqueous solution at desired pH, ionic strength, etc.). As further described in the Examples, below, for the interface formed between water and α-quartz, the orientation angle which maximizes the constructive interference is 30° from the reference axis. Alternatively, the selected orientation angle may be that which substantially maximizes the destructive interference of the bulk second harmonic signal and the interfacial second harmonic signal. By "maximizes" it is meant "substantially maximizes" such that the destructive interference does not be at its perfect maximum. As further described in the Examples, below, for the interface formed between water and α-quartz, this orientation angle is 90° from the reference axis. However, other orientation angles may be used. The method may further comprise subsequently carrying out the illumination and detection steps at additional, different orientation angles. This may be useful to serve as a check for possible artifacts or measurement errors.

The present methods may include a variety of other steps, depending upon the desired interfacial electrostatic information to be extracted. For example, the steps of the present methods may be carried out as part of a charge-screening experiment in which SHG signals are also collected while changing the concentration of an electrolyte added to the sample.

In a conventional charge-screening experiment, non-resonant SHG signals (i.e., by using non-resonant light) can be generated and detected from an interface of interest. The intensity of the SHG signal is sensitive to the interfacial potential according to Equation (1):

$$\sqrt{I_{SHG}} = E_{2\omega} \propto P_{2\omega} = \chi^{(2)} E_\omega E_\omega + \chi^{(3)} E_\omega E_\omega \Phi_0 \quad (1)$$

wherein $I_{SHG}$ is the intensity of the SHG signal, E is the electric field at a given frequency, $\chi^{(2)}$ and $\chi^{(3)}$ are the second and third nonlinear susceptibilities, and $\Phi_0$ is the interfacial potential. Equation (1) can be represented as $A + B\,\Phi_0$, wherein A and B include the second and third order terms, respectively. A variety of models of interfacial potential may be used. An illustrative model is the Gouy-Chapman model given by Equation (2):

$$\Phi_0 = \frac{2k_B T}{ze} \sinh^{-1}\left[\frac{\sigma}{\sqrt{8000 k_B T \varepsilon_0 \varepsilon_r C}}\right] \quad (2)$$

wherein z is the valence of the electrolyte, T is the temperature, $\varepsilon_0$ and $\varepsilon_r$ are the permittivities of the vacuum and medium, respectively, σ is the surface charge density, and C is the bulk electrolyte concentration. The SHG electric field (denoted as either $E_{2\omega}$ or $E_{SHG}$) can be extracted from the detected SHG signals, the $E_{SHG}$ values plotted as a function of bulk electrolyte concentration C, and the data fit using combined Equations (1) and (2) with A, B and σ as fitting parameters. However, such fitting relies on the knowledge of the sign of the nonlinear susceptibilities in Equation (1). Knowledge of this sign, and thus the sign of the surface charge requires a reference measurement.

By contrast to conventional methods employing external phase references or additional measurements as described above, the present methods make use of the noncentrosymmetric material as an internal phase reference. By measuring the sign of the interference (i.e., constructive or destructive) between the bulk second harmonic signal (from the α-quartz substrate) and the interfacial second harmonic signal at a specific orientation angle(s) of the α-quartz substrate, one can determine the sign of the interfacial charge directly, in a single, modified charge-screening experiment.

Additional illustrative embodiments of the present methods are as follows. First, a laser beam (or laser beams) are focused into the interface of interest (e.g., the illustrative aqueous solution/thin film interface shown in FIG. 5B). Several illumination geometries are possible, including the external reflection geometry described in the Examples below, as well as crossed-beam geometries or counter-propagating geometries, etc. Next, it is tested whether the SHG signal intensity changes by varying pH or salt concentration in the aqueous solution. If it doesn't, the solution conditions are such that the interface of interest is net neutral, i.e. it either contains no charged surface sites entirely, or the number of positively and negatively charged surface sites is equal. This condition is generally referred to as the point of zero charge for materials that are, for instance, amphoteric. Thus, such an embodiment can determine the point of zero charge for a variety of materials.

If the SHG signal intensity changes upon pH or ionic strength variation, one may probe a charged surface and the steps of the present methods may be combined with those of a charge-screening experiment. The noncentrosymmetric material (e.g., α-quartz) is aligned to a selected orientation angle (e.g., 30°) and the salt concentration may be sequentially increased while taking data points (i.e., detecting SHG signal as a function of increasing salt concentration). Whether the SHG signal increases or decreases determines the charge of the interface of interest as further described below.

Figure 4:
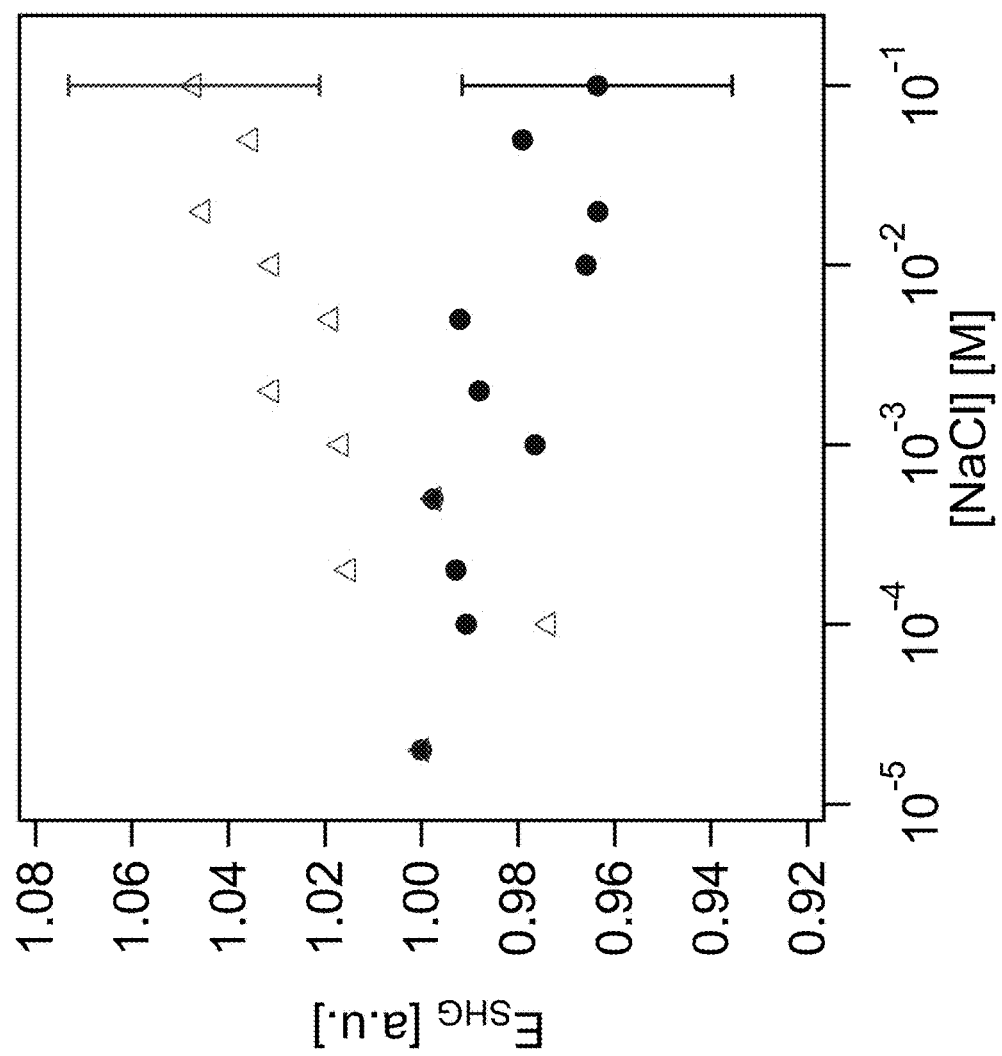
FIG. 4 shows the results of the salt screening experiment described in the Examples. SHG intensity from the α-quartz/water interface maintained at pH 7 during conditions of dynamically changing bulk solution ionic strength varying between $10^{-5}$ and $10^{-1}$ M NaCl. Error bars represent one standard deviation, with six (respectively nine) measurements for the $\varphi=75°$ (respectively 15°) series.

In particular, whether interference between the bulk second harmonic signal and the interfacial second harmonic signal is constructive or destructive for a selected orientation angle of the α-quartz is controlled by the phase of the interfacial second harmonic signal with respect to the second harmonic signal from the bulk α-quartz. This phase is determined by the polarization of the water molecules, which is ultimately determined by the charge of the surface. As shown in the Examples below, it is known that α-quartz is negatively charged and that it produces constructive interference from a water/α-quartz interface at 30° from the reference axis. Thus, the water/α-quartz interface may be used as a reference interface in analyzing the behavior of the SHG signal from an interface of interest. If the interface of interest also produces constructive interference at this orientation angle, it follows that the interface of interest is also negatively charged. If the interface of interest instead produces destructive interference at this orientation angle, it follows that the interface of interest is positively charged. Similarly, if the SHG signal from the interface of interest decreases with increasing ionic strength at the 30° orientation angle, it follows that the interface was also initially negatively charged. If the SHG signal increases with increasing ionic strength at the 30° orientation angle, it follows that the interface of interest was instead initially positively charged. These conclusions are based on the fact that the SHG signal from a water/α-quartz interface at 30° (the reference interface) decreases with increasing ionic strength; see FIG. 4, circles.

Apparatuses and systems for carrying out the present methods are also provided. An apparatus may include a sample cell configured to support a noncentrosymmetric material and to contain/support a material in contact with the noncentrosymmetric material and optics configured to illuminate the interface of the noncentrosymmetric material and the material with light having a frequency co. The sample cell may be configured to change the orientation angle of the noncentrosymmetric material. The apparatus may be incorporated into a system as shown in FIG. 1A, the apparatus/system including various additional components typically used in SHG spectroscopy, e.g., detectors, light sources, controllers, etc.

Illustrative applications for the present methods, apparatuses and systems include surface potential measurements, streaming potential measurements, point of zero charge measurements, over-under-charging measurements, membrane charge and potential measurements, and polymer coating charge and potential measurements.

EXAMPLES

Introduction

Probing the polarization of water molecules at charged interfaces by second harmonic generation (SHG) spectroscopy has been heretofore limited to isotropic materials. In this Example, non-resonant nonlinear optical measurements at the interface of anisotropic z-cut α-quartz and water under conditions of dynamically changing ionic strength and bulk solution pH are reported. It is found that the product of the third-order susceptibility and the interfacial potential, $\chi^{(3)}\Phi$ (0), is given by $\chi^{(3)} - i\chi'^{(3)})\Phi(0)$, and that the interference between this product and the second-order susceptibility of bulk quartz depends on the rotation angle of α-quartz around the z-axis. The experiments show that this newly identified term, $i\chi'^{(3)}\Phi(0)$, which is out of phase from the surface terms, is of bulk origin. Internally phase referencing the interfacial response for the interfacial orientation analysis of species or materials in contact with α-quartz is discussed along with the implications for conditions of resonance enhancement.

In this Example, an experimental geometry is used that produces considerable non-resonant SHG signal intensity from the z-cut α-quartz/water interface in the presence of bulk SHG signals from both the quartz and the electrical double layer under conditions of dynamically varying pH and ionic strength. The approach, which uses an external reflection geometry, femtosecond laser pulses having just nanojoule pulse energies, and a high repetition rate, enables the experimental identification a source of surface potential induced bulk SHG from the electrical double layer. Further, it expands the scope of SHG spectroscopy to probe interfaces of non-centrosymmetric materials and establishes phase referenced SHG spectroscopy to buried interfaces by using z-cut α-quartz as an internal phase standard.

Methods

Sample Information. In the experiments, three different right-handed, z-cut α-quartz samples (10 mm diameter, 3 mm thick) from three different vendors were used: Meller Optics (Providence, R.I.); Knight Optical (North Kingston, R.I.); and Precision Micro-Optics (Woburn, Mass.). The fused silica sample was purchased from Meller Optics. Prior to measurements, the samples were treated for 1 hour with NoChromix solution (Godax Laboratories), a commercial glass cleaner (caution: NoChromix should only be used after having read and understood the relevant safety information). The samples were then sonicated in methanol for six minutes, sonicated in Millipore water for six minutes, dried in a 100° C. oven, and plasma cleaned (Harrick Plasma) for 30 seconds on the highest setting. This procedure produces surfaces that are void of vibrational SFG responses in the C—H stretching region[26].

Determining Crystal Orientation. Due to the dependence of the $I_{SHG}$ response on the orientational angle of the α-quartz crystal sample, it was necessary to unambiguously identify the crystal orientation used in the experiments. In this study, φ was defined to be the clockwise rotation of the crystal about its z-axis, measured from its +x-axis (i.e. at 0° the incoming laser beam is aligned with its horizontal projection along the +x-axis of the α-quartz crystal, at 30° the crystal has been rotated 30° clockwise, etc). The x-axis of the crystal can be determined by finding the $I_{SHG}$ maximum in the PP polarization combination or the $I_{SHG}$ minimum in the PS polarization combination[17] (data not shown) while rotating the crystal about its axis. Determining the orientation of the x-axis, i.e. whether the incoming laser beam is aligned parallel or anti-parallel with the x-axis, is more difficult. Possible techniques include measuring the sign of the small voltage produced upon deformation of the crystal due to its piezoelectricity,[36] determining whether the bulk signal constructively or destructively interferes with the SFG C—H stretching signal from alkane chain monolayers absorbed on the interface,[17] or obtaining Laue diffraction patterns from the α-quartz crystal. Laue diffraction patterns from an α-quartz crystal of known orientation (provided by the supplier) were compared with that of the unknown sample in order to determine its absolute orientation (data not shown). Two commercial α-quartz samples for which the suppliers (Knight Optical and PM Optics) had determined the absolute crystal orientation were also tested. The same SHG responses were obtained across all three samples.

Laser Setup. The p-polarized 800 nm output of a Ti:Sapphire oscillator (Mai Tai, Spectra-Physics, 100 fs pulses, λ=800 nm, 82 MHz) was focused through a hollow fused quartz dome onto the interface between water and the solid substrate in the external reflection geometry depicted in FIG. 1A. Prior to the sample stage, the beam was passed through a long-pass filter to remove any second harmonic co-propagating with the fundamental beam, attenuated with a variable density filter to 0.50±0.01 W, passed through a half-wave plate for input polarization control, and focused onto the α-quartz/water or fused silica/water interface at an angle of 60°. The beam waist in the focal region was estimated at 30 μm in diameter.

The SHG signal was recollimated, passed through a 400 nm bandpass filter (FBH400-40, Thor Labs), and directed through a polarizer and monochromator for detection via a Hamamatsu photomultiplier tube connected to a preamplifier (SR445A, Stanford Research Systems) and a single photon counter (SR400, Stanford Research Systems).[26] A portion of the fundamental beam was picked off prior to the sample stage and continuously monitored by a power meter (Newport 1917-R) during acquisitions to allow for continuous normalization of signal intensity to power and account for the impact of slight, albeit unavoidable, laser power fluctuations on the SHG signal intensity. Compared to internal reflection, SHG signals obtained using the present geometry are generally ~400 times more sensitive to the interface relative to the bulk. This is shown in Table 1, below. The internal reflection geometry gives higher signal intensities from both the bulk α-quartz and the fused silica surface at pH 11.5. However, if it is assumed that the fused silica and α-quartz surfaces have roughly comparable signal intensities at pH 11.5, it can be seen that the ratio of expected surface signal intensity to bulk signal intensity for α-quartz is more favorable in the external reflection geometry.

TABLE 1

Typical ISHG in internal and external reflection geometries.

| Substrate | Internal Reflection | External Reflection |
| --- | --- | --- |
| α-quartz | 1,500,000 | 1,000 |
| Fused silica | 200 | 50 |
| Ratio | 7,500 | 20 |

It is noted that geometries in which 100-femtosecond pulses from a kHz amplifier laser system accessed the quartz/water interface through bulk quartz as thin as 200 μm (i.e. the inverted geometry of what is depicted in FIG. 1A) were not successful, even when applying a second quartz plate for background suppression.[37]

Solution Preparation.

The aqueous solutions were prepared using Millipore water (18.2 MΩ/cm) and NaCl (Alfa Aesar, 99+%). The pH of the solutions was adjusted using dilute solutions of HCl (E.M.D., ACS grade) and NaOH (Sigma Aldrich, 99.99%) and verified using a pH meter.

Figure 2:
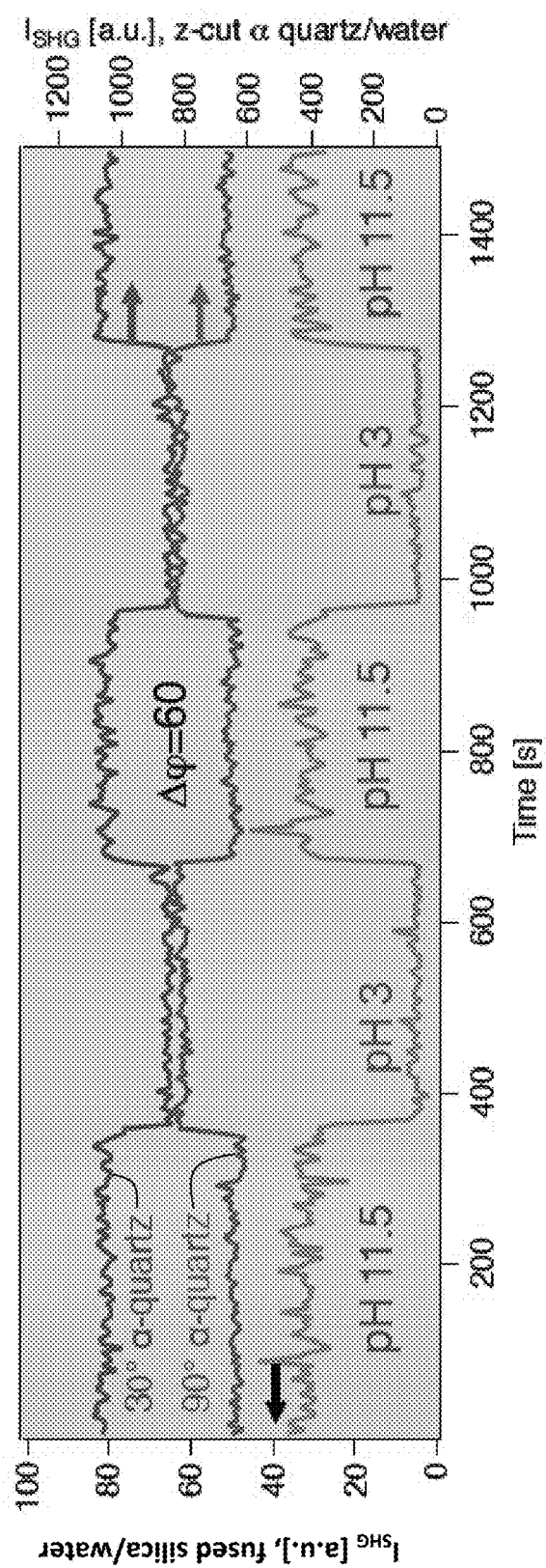
FIG. 2 shows the results of pH Jump experiments described in the Examples. SHG intensity in counts per second obtained from the fused silica/water (bottom trace, left y-axis) and α-quartz/water (top traces, right y axis) interfaces under conditions of dynamically changing bulk solution pH varying between 3 and 11.5. Top two traces indicate results obtained with 60° difference in α-quartz rotational angle. The constructive and destructive interference observed for the α-quartz/water interface confirm interference between the potential-dependent interfacial and bulk quartz terms of the nonlinear susceptibility.

Results pH Jumps Over Silica and Quartz/Water Interfaces. Using a dual-pump flow system[26], the pH of the aqueous phase was transitioned between pH 3 and 11.5 so as to probe the interfacial potential dependence of the SHG responses. Near the point of zero charge, reported variously in the literature as pH 2.227 and pH 2.628 for α-quartz and pH 2.3 for fused silica[29], little SHG signal from the interface is expected, whereas the considerable negative interfacial potential at pH 11.5 should yield considerable SHG signal intensity[1,26]. FIG. 2 shows the SHG vs time traces obtained from the fused silica/water interface using the flow cell shown in FIG. 1A. Indeed, the same increases are observed (respectively decreases) in SHG signal intensity upon increasing (respectively decreasing) the bulk solution pH that we previously reported for fused silica using a total internal reflection geometry (FIG. 6A).[26] At 3 mM total salt concentration, SHG signal intensities generally range between 5 and 10 counts per second at pH 3, and between 30 and 40 counts per second at pH 11.5. Upon replacing the fused silica window with right-handed z-cut α-quartz oriented 30° from the +x-axis (see Methods), the same response is observed, albeit with a large bulk signal intensity leading to both significantly larger overall signal intensities and variations in signal intensity with varying pH.

Figure 3:
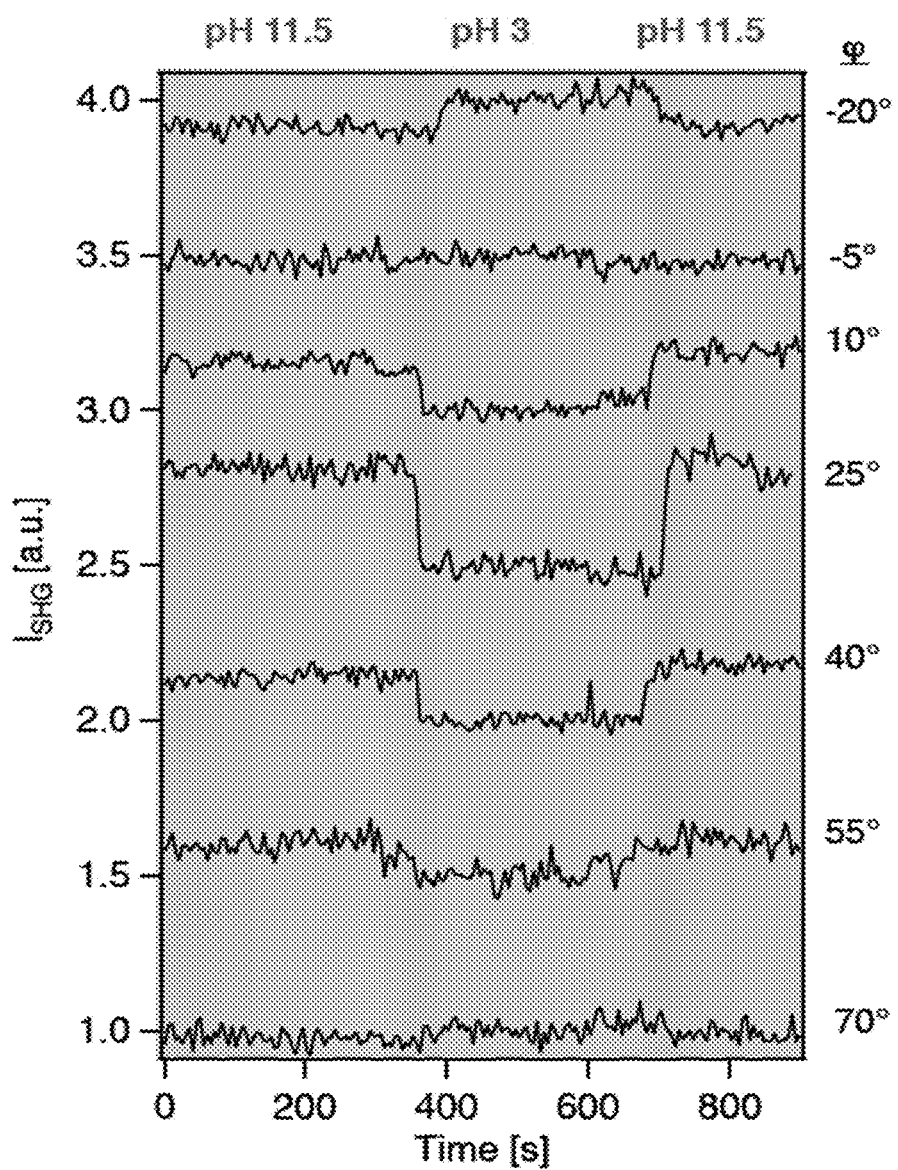
FIG. 3 shows the results of the interference experiment described in the Examples. SHG intensity vs time traces normalized to intensity at pH 3 obtained from the α-quartz/water interface at different rotational angles of the α-quartz crystal during conditions of dynamically changing bulk solution pH varying between 3 and 11.5.

Rotating Quartz Orientation Angle Reveals Interference. FIG. 2 shows that the change in the SHG intensity observed for high vs. low pH flips sign upon rotation of the quartz crystal by 60° around the z-axis, indicating modulation between negative and positive interference with the $\chi^{(2)}$ term of the bulk quartz. The P-in/P-out polarization combination (termed "PP" hereafter) was selected as it demonstrated the highest interfacial sensitivity out of the PP, PS, 45P, and 45S polarization combination (data not shown). FIG. 3 further shows that the constructive and destructive interference of the SHG signal depends on changing crystal rotation angles for the p-in/p-out polarization combination. Data showing the $\Delta I_{SHG}$ as a function of quartz rotational angle were obtained (data not shown). Because in this geometry the beams must propagate through the dynamically changing aqueous phase, the dependence of the observed changes in the SHG intensity on the rotational angle of the α-quartz substrate indicates their origin as the interface and not changing optical properties of the aqueous phase, which would not depend on the angle of the α-quartz substrate. Additional control experiments show invariance of the results with minor variations in focal lens position and quadratic dependence of the $I_{SHG}$ on laser power (data not shown).

DISCUSSION

The constructive and destructive interference seen in FIGS. 2 and 3 can be understood by recalling that the non-resonant SHG or SFG signal from bulk α-quartz is a purely imaginary term[30,31]. This property of α-quartz has been employed to provide an internal phase standard that can amplify and interfere with the imaginary part of the vibrational SFG spectra of molecular surface species[18,32]. Yet, when the surface second order susceptibility is non-resonant, i.e., all the surface response terms are purely real, interference with the imaginary term of the bulk α-quartz response cannot occur. However, the observations shown in FIG. 2 demonstrate that the non-resonant SHG signal from the water/α-quartz interface is subject to interference from the non-resonant SHG signal from the bulk α-quartz, indicating a new source of surface potential-induced bulk SHG from the aqueous solution.

The observed interference shown in FIG. 2 can be rationalized by considering that the phase of the bulk SHG signal produced by α-quartz shifts by 180° when the crystal is rotated clockwise by 60° around the z-axis (the sign of the bulk quartz phase is depicted in FIG. 1B). Rotation is shown to change the coherent interaction between the interfacial signal and bulk signal from constructive to destructive interference, as is expected from a 180° phase shift in the bulk quartz $\chi^{(2)}$ term[32]. This behavior can be mathematically treated according to the following equation:

$$I_{SHG} \propto |\chi^{(2)} + (\chi_1^{(3)} - i\chi_2^{(3)})\Phi(0) \pm i\chi_{bulk\ quartz}^{(2)}|^2 \qquad (3)$$

where the sign of the $\pm i\chi_{bulk\ quartz}^{(2)}$ term is controlled by the rotational angle of the α-quartz crystal. Here, $\chi_1^{(3)}$ and $i\chi_2^{(3)}$ are related by a phase matching factor as described below. Even though the $\chi^{(3)}$ mechanism for interfacial potential-induced second harmonic generation has been long established[1], the importance of phase matching in the $\chi^{(3)}$ term has only recently been theoretically considered[33]. An experimental validation requires a phase-referenced measurement, like the one demonstrated and established herein.

Figure 7:
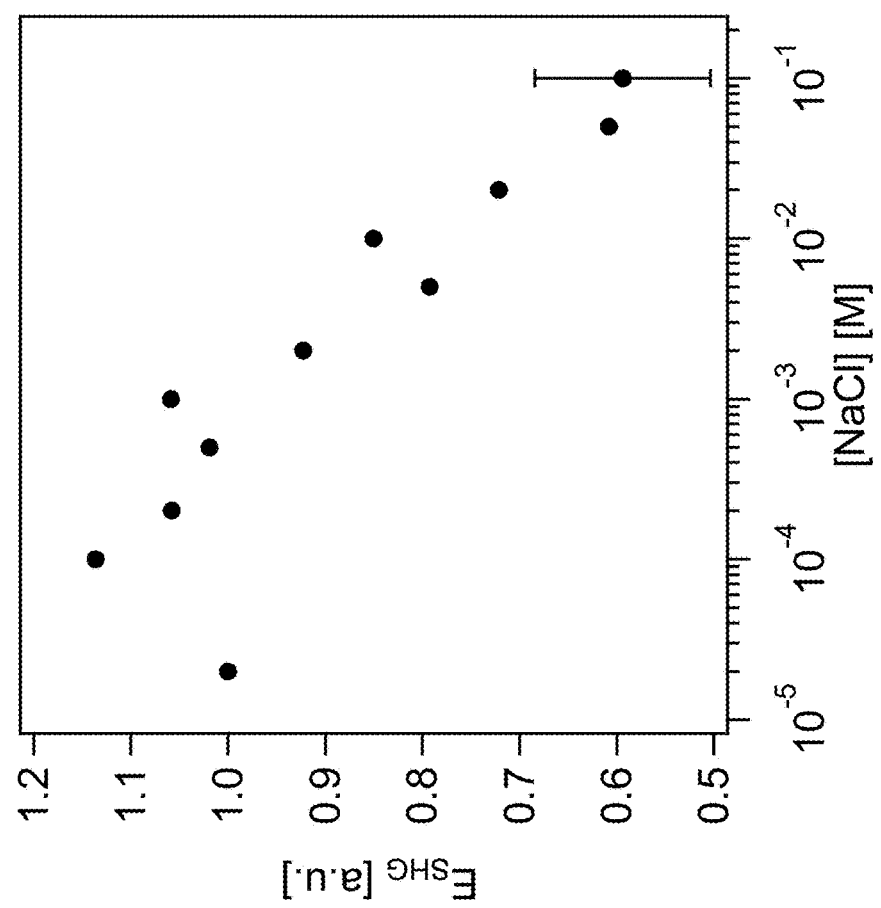
FIG. 7 shows the SHG intensity from a fused silica/water interface maintained at pH 7 during conditions of dynamically changing bulk solution ionic strength varying between $10^{-5}$ and $10^{-1}$ M NaCl. Interfacial potential and charge screening properties of the fused silica/water interface are comparable to those of the α-quartz/water interface, though the SHG signal lacks the bulk $\chi^{(2)}$ of the α-quartz due to the centrosymmetric nature of fused silica. This allows direct comparison to FIG. 4. Error bars represent one standard deviation with three measurements.

As further confirmation that the observed changes in the SHG signal intensity with pH are attributable to the interface, SHG signal intensities at pH 7 were recorded under conditions of increasing ionic strength for two quartz crystal rotation angles differing by 60°. For a charged interface, increases in the ionic strength result in screening of the interfacial charges, thus reducing the interfacial potential to which the water molecules in the electrical double layer are subjected, and ultimately the associated SHG signal intensity[5,34]. Indeed, this behavior is observed for both fused silica (FIG. 7) and α-quartz (FIG. 4, circles), at ionic strengths above ~$10^{-4}$ M NaCl, with opposite behavior (increases in the ionic strength coincide with SHG intensity increases) observed upon rotating the crystallographic axis of the z-cut quartz by 60° (FIG. 4, triangles), as is observed in the pH jump experiments. Thus, the constructive and destructive interference discovered here for the α-quartz/water interface is confirmed.

The findings greatly expand the scope of SHG spectroscopy beyond amorphous and centrosymmetric materials and towards crystal classes that lack centrosymmetry, including the more than 500 non-centrosymmetric oxides catalogued to date[35]. In doing so, they enable directly comparing the amphoteric properties of amorphous and crystalline materials, such as fused silica and α-quartz. Using an SHG bulk signal as an internal reference from which phase information of the surface signal, and therefore orientation information at the interface can be determined, is highly advantageous. The use of thin film deposition techniques such as atomic layer deposition, electron beam deposition, or spin-coating, or surface functionalization methods such as silane chemistry, directly on α-quartz, or other reference materials with known phase and second-order susceptibilities, enables using phase referenced SHG spectroscopy as a method for unambiguously determining the sign (+ or −) of surface charges. A thin film with a thickness of only a few nm interacts with water molecules in a similar fashion to the surface of its bulk material, yet still allows coherent interaction between the second harmonic signal generated at the interface and the bulk signal produced by the α-quartz substrate. Likewise, a thin film of a nonlinear optical crystal with a known phase grown on fused silica or another optically transparent centrosymmetric medium would allow for the presence of an internal phase standard with an acceptable SHG intensity without requiring propagation through an aqueous medium. For conditions of electronic or vibrational resonance, it is noted that the absorptive (imaginary) and dispersive (real) terms of $\chi^{(2)}$, $\chi_1^{(3)}$ and $\chi_2^{(3)}$ may mix.

Derivation of the Origin of the $i\chi_2^{(3)}$ Term, See Also Refs. 32 and 33. As the electric field $E_{dc}(z) = -d\Phi(z)/dz$ is z (depth)-dependent and there is the phase matching factor that is also z dependent, one has:

$$\chi_{dc}^{(2)} = \int_0^\infty \chi^{(3)} E_{dc}(z) e^{-i\Delta k_z z} dz \qquad (Eq.\ 1)$$

$$= \int_0^\infty -\chi^{(3)} \frac{d\Phi(z)}{dz} e^{-i\Delta k_z z} dz$$

$$= -\chi^{(3)} \Phi(z) e^{-i\Delta k_z z} \Big|_0^\infty + \chi^{(3)} \int_0^\infty \Phi(z)(-i\Delta k_z) e^{-i\Delta k_z z} dz$$

$$= \chi^{(3)} \Phi(0) - i\Delta k_z \chi^{(3)} \int_0^\infty \Phi(z) e^{-i\Delta k_z z} dz$$

Here, $1/\Delta k_z$ is the coherence length of the SHG or SFG process, $\Phi(\infty) = 0$, and the following integration relationship was used:

$$\int \frac{df(z)}{dz} g(z) dz = f(z)g(z) - \int f(z) \frac{dg(z)}{dz} dz \qquad (Eq.\ 2)$$

A good approximation is that $\Phi(z) = \Phi(0)e^{-kz}$, where $1/k$ is the Debye screening length factor. Then, $$\chi_{dc}^{(2)} = \chi^{(3)} \Phi(0) - i\Delta k_z \chi^{(3)} \int_0^\infty \Phi(0) e^{-kz} e^{-i\Delta k_z z} dz$$

$$= \chi^{(3)} \Phi(0) + \frac{-i\Delta k_z}{k + i\Delta k_z} \chi^{(3)} \Phi(0)$$

$$= \frac{k}{k + i\Delta k_z} \chi^{(3)} \Phi(0)$$

Therefore, in the total effective surface susceptibility, $$\chi_{eff}^{(2)} = \chi^{(2)} + \chi_{dc}^{(2)} = \chi^{(2)} + (\chi_1^{(3)} - i\chi_2^{(3)}) \Phi(0) \qquad (Eq.\ 3)$$

one has $$\chi_1^{(3)} = \frac{k^2}{k^2 + (\Delta k_z)^2} \chi^{(3)} \qquad (Eq.\ 4.1)$$

$$\chi_2^{(3)} = \frac{k\Delta k_z}{k^2 + (\Delta k_z)^2}\chi^{(3)} \qquad (Eq.\ 4.2)$$

Therefore, because the surface field is real and the phase matching factor is complex, the total $\chi_{dc}^{(2)}=(\chi_1^{(3)}-i\chi_2^{(3)})\Phi(0)$ contribution is complex.

When $k \ll \Delta k_z$, i.e. the Debye length is long (low electrolyte concentration), one finds $$\chi_1^{(3)}\sim 0 \text{ and } \chi_2^{(3)}\sim \frac{k}{\Delta k_z}\chi^{(3)} \qquad (Eq.\ 5.1)$$

and the dc contribution is essentially imaginary.

When $k \gg \Delta k_z$, i.e. the Debye length is very small (high electrolyte concentration), one finds $$\chi_1^{(3)}\sim \chi^{(3)} \text{ and } \chi_2^{(3)}\sim \frac{\Delta k_z}{k}\chi^{(3)}\sim 0 \qquad (Eq.\ 5.2)$$

and the real term dominates.

When $k \sim \Delta k_z$, i.e. the Debye length and phase matching coherent length are comparable, the real and imaginary terms for the $\chi^{(3)}$ are comparable.

The derivation above assumes that the surface potential is of the form $\Phi(z)=\Phi(0)e^{-kz}$. The actual surface potential may be different from this form, but essentially it decays when moving away from the surface. In addition, the surface potential can not only induce bulk $\chi^{(3)}$ responses from the water side, but also from the fused silica or the $\alpha$-quartz side. (See Bethea, C. G. Electric field induced second harmonic generation in glass. *Appl. Optics* 14, 2435-2437 (1975).) Nevertheless, the following relationship, as established herein, should generally hold:

$$\chi_{\text{eff}}^{(2)}=\chi^{(2)}+\chi_{dc}^{(2)}=\chi^{(2)}+(\chi_1^{(3)}-i\chi_2^{(3)})\Phi(0) \qquad (Eq.\ 6)$$

REFERENCES

1. Ong, S. W., Zhao, X. L. & Eisenthal, K. B. Polarization of water molecules at a charged interface: second harmonic studies of the silica/water interface. *Chemical Physics Letters* 191, 327-335 (1992).
2. Eisenthal, K. B. Liquid Interfaces Probed by Second-Harmonic and Sum-Frequency Spectroscopy. *Chem. Rev.* 96, 1343-1360 (1996).
3. Eisenthal, K. B. Second Harmonic Spectroscopy of Aqueous Nano- and Microparticle Interfaces. *Chem. Rev.* 106, 1462-1477 (2006).
4. Geiger, F. M. Second Harmonic Generation, Sum Frequency Generation, and $\chi^{(3)}$: Dissecting Environmental Interfaces with a Nonlinear Optical Swiss Army Knife. *Annual Review of Physical Chemistry* 60, 61-83 (2009).
5. Hayes, P. L., Malin, J. N., Jordan, D. S. & Geiger, F. M. Get charged up: Nonlinear optical voltammetry for quantifying the thermodynamics and electrostatics of metal cations at aqueous/oxide interfaces. *Chemical Physics Letters* 499, 183-192 (2010).
6. Sauerbeck, C., Braunschweig, B. & Peukert, W. Surface Charging and Interfacial Water Structure of Amphoteric Colloidal Particles. *J. Phys. Chem. C* 118, 10033-10042 (2014).
7. Zhao, X., Ong, S., Wang, H. & Eisenthal, K. B. New method for determination of surface pKa using second harmonic generation. *Chem. Phys. Lett.* 214, 203-207 (1993).
8. Boyd, R. W. *Nonlinear Optics*, 3rd Edition. (Elsevier Academic Press Inc, 2008).
9. Chang, R. K., Ducuing, J. & Bloembergen, N. Relative Phase Measurement Between Fundamental and Second-Harmonic Light. *Phys. Rev. Lett.* 15, 6-8 (1965).
10. Lu, R., Rao, Y., Zhang, W.-k. & Wang, H.-f in SPIE International Symposium on Optical Science and Technology. 115-124.
11. Mifflin, A. L., Musorrafiti, M. J., Konek, C. T. & Geiger, F. M. Second Harmonic Generation Phase Measurements of Cr(VI) at a Buried Interface. *J. Phys. Chem. B* 109, 24386-24390 (2005).
12. Kemnitz, K., Bhattacharyya, K., Hicks, J. M., Pinto, G. R., Eisenthal, B. & Heinz, T. F. The phase of second-harmonic light generated at an interface and its relation to absolute molecular orientation. *Chemical Physics Letters* 131, 285-290 (1986).
13. Superfine, R., Huang, J. Y. & Shen, Y. R. Phase measurement for surface infrared-visible sum-frequency generation. *Opt. Lett.* 15, 1276-1278 (1990).
14. Vanselous, H. & Petersen, P. B. Extending the Capabilities of Heterodyne-Detected Sum-Frequency Generation Spectroscopy: Probing Any Interface in Any Polarization Combination. *J. Phys. Chem. C* 120, 8175-8184 (2016).
15. Wang, J., Bisson, P. J., Marmolejos, J. M. & Shultz, M. J. Measuring Complex Sum Frequency Spectra with a Nonlinear Interferometer. *J. Phys. Chem. Lett.* 7, 1945-1949 (2016).
16. Myalitsin, A., Urashima, S.-h., Nihongyanagi, S., Yamaguchi, S. & Tahara, T. Water Structure at the Buried Silica/Aqueous Interface Studied by Heterodyne-Detected Vibrational Sum-Frequency Generation. *J. Phys. Chem. C* 120, 9357-9363 (2016).
17. Fu, L., Chen, S.-L. & Wang, H.-F. Validation of Spectra and Phase in Sub-1 cm-1 Resolution Sum-Frequency Generation Vibrational Spectroscopy through Internal Heterodyne Phase-Resolved Measurement. *J. Phys. Chem. B* 120, 1579-1589 (2015).
18. Ostroverkhov, V., Waychunas, G. A. & Shen, Y. R. New information on water interfacial structure revealed by phase-sensitive surface spectroscopy. *Phys. Rev. Lett.* 94, 046102 (2005).
19. Stumm, W. & Morgan, J. J. *Aquatic Chemistry, Chemical Equilibria and Rates in Natural Waters*. 3rd edn, (John Wiley & Sons, 1996).
20. Al-Abadleh, H. A. & Grassian, V. H. Oxide Surfaces as Environmental Interfaces. *Surf. Sci. Rep.* 52, 63-162 (2003).
21. Blacic, J. D. Plastic-deformation mechanisms in quartz: The effect of water. *Tectonophysics* 27, 271-294 (1975).
22. Gaigeot, M.-P., Sprik, M. & Sulpizi, M. Oxide/water interfaces: how the surface chemistry modifies interfacial water properties. *J. Phys.: Condens. Matter* 24, 124106 (2012).
23. Ostroverkhov, V., Waychunas, G. A. & Shen, Y. R. Vibrational spectra of water at water/$\alpha$-quartz (0 0 0 1) interface. *Chem. Phys. Lett.* 386, 144-148 (2004).
24. Cimas, A., Tielens, F., Sulpizi, M., Gaigeot, M.-P. & Costa, D. The amorphous silica-liquid water interface studied by ab initio molecular dynamics (AIMD): local organization in global disorder. *J. Phys.: Condens. Matter* 26, 244106 (2014).

25. Liu, Y., Dadap, J. I., Zimdars, D. & Eisenthal, K. B. Study of interfacial charge transfer complex on TiO2 particles in aqueous suspension by second-harmonic generation. *Journal of Physical Chemistry B* 103, 2480-2486 (1999).
26. Achtyl, J. L., Unocic, R. R., Xu, L., Cai, Y., Raju, M., Zhang, W., . . . & Geiger, F. M. Aqueous proton transfer across single-layer graphene. *Nature Communications* 6 (2015).
27. Parks, G. A. The Isoelectric Points of Solid Oxides, Solid Hydroxides, and Aqueous Hydroxo Complex Systems. *Chemical Reviews* 65, 177-198 (1965).
28. Rusch, B., Hanna, K. & Humbert, B. Coating of quartz silica with iron oxides: Characterization and surface reactivity of iron coating phases. *Colloids and Surfaces A: Physicochemical and Engineering Aspects* 353, 172-180 (2010).
29. Kosmulski, M. The pH-dependent surface charging and points of zero charge: V. Update. *Journal of Colloid and Interface Science* 353, 1-15 (2011).
30. Byrnes, S. J., Geissler, P. L. & Shen, Y. R. Ambiguities in surface nonlinear spectroscopy calculations. *Chemical Physics Letters* 516, 115-124 (2011).
31. Bloembergen, N. & Pershan, P. S. Light Waves at the Boundary of Nonlinear Media. *Physical Review* 128, 606-622 (1962).
32. Fu, L., Chen, S. & Wang, H.-F. Validation of Spectra and Phase in Sub-1 cm-1 Resolution Sum-Frequency Generation Vibrational Spectroscopy Through Internal Heterodyne Phase Resolved Measurement. *The Journal of Physical Chemistry B* (2015).
33. Gonella, G., Litgebaucks, C., de Beer, A. G. F. & Roke, S. Second Harmonic and Sum Frequency Generation from Aqueous Interfaces is Modulated by Interference. *J Phys. Chem. C* 120, 9165-9173 (2016).
34. Yan, E. C. Y., Liu, Y. & Eisenthal, K. B. New Method for Determination of Surface Potential of Microscopic Particles by Second Harmonic Generation. *J. Phys. Chem. B* 102, 6331-6336 (1998).
35. Halasyamani, P. S. & Poeppelmeier, K. R. Noncentrosymmetric Oxides. *Chem. Mat.* 10, 2753-2769 (1998).
36. Nowakowski, P. J., Woods, D. A., Bain, C. D. & Verlet, J. R. R. Time-resolved phase-sensitive second harmonic generation spectroscopy. *The Journal of Chemical Physics* 142, 084201 (2015).
37. Saslow, S. A. *Geochemical Interfaces and Metal Contaminant Transport Studied by Second Harmonic Generation*, Chapter 5, Developing SHG as a Technique for Probing the Interface of Non-Centrosymmetric Media with Water: Acid-Base Chemistry of the α-Quartz/Water Interface, PhD thesis, Northwestern University, (2015).

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method of probing an interface, the method comprising:
   (a) illuminating an interface formed between a noncentrosymmetric material having a selected orientation angle with respect to a reference axis and a different material, or formed between two different materials and disposed over the noncentrosymmetric material, with light having a frequency ω under conditions to generate a second harmonic generation (SHG) signal having frequency 2ω, and
   (b) detecting the SHG signal, the SHG signal comprising a bulk second harmonic signal from the noncentrosymmetric material and an interfacial second harmonic signal from the interface.

2. The method of claim 1, further comprising (c), comparing the detected SHG signal to a SHG signal generated from a reference interface formed between the noncentrosymmetric material and a reference material at the selected orientation angle.

3. The method of claim 1, wherein the noncentrosymmetric material is α-quartz.

4. The method of claim 1, wherein the noncentrosymmetric material is provided as a substrate composed entirely of the noncentrosymmetric material.

5. The method of claim 1, wherein the noncentrosymmetric material is provided as a film on a supporting substrate.

6. The method of claim 5, wherein the supporting substrate comprises a centrosymmetric material.

7. The method of claim 1, wherein the different material, or one of the two different materials, comprises water.

8. The method of claim 1, wherein the interface is the interface formed between the two different materials.

9. The method of claim 8, wherein one of the two different materials comprises water.

10. The method of claim 8, wherein one of the two different materials is a film formed on the noncentrosymmetric material.

11. The method of claim 10, wherein the other of the two different materials comprises water.

12. The method of claim 1, wherein the light is non-resonant light.

13. The method of claim 1, wherein step (a) is carried out using an external reflection geometry.

14. The method of claim 1, further comprising repeating steps (a) and (b) at a second, different orientation angle.

15. The method of claim 1, wherein the different material, or one of the two different materials, comprises water, and the method further comprises carrying out steps (a) and (b) under conditions of changing ionic strength, changing pH, or both.

* * * * *